(12) United States Patent
Gu et al.

(10) Patent No.: US 11,556,805 B2
(45) Date of Patent: Jan. 17, 2023

(54) COGNITIVE DATA DISCOVERY AND MAPPING FOR DATA ONBOARDING

(71) Applicant: International Business Machines Corporation, Armonk, NY (US)

(72) Inventors: Yu Gu, Austin, TX (US); Dingcheng Li, Rochester, MN (US); Pei Ni Liu, Beijing (CN); Xiao Xi Liu, Beijing (CN); Daniel Dean, Yorktown Heights, NY (US); Yaoping Ruan, White Plains, NY (US); Jing Min Xu, Beijing (CN)

(73) Assignee: International Business Machines Corporation, Armonk, NY (US)

( * ) Notice: Subject to any disclaimer, the term of this patent is extended or adjusted under 35 U.S.C. 154(b) by 917 days.

(21) Appl. No.: 15/900,892

(22) Filed: Feb. 21, 2018

(65) Prior Publication Data

US 2019/0258942 A1 Aug. 22, 2019

(51) Int. Cl.
*G06N 5/02* (2006.01)
*G06N 20/00* (2019.01)
*G06F 16/25* (2019.01)

(52) U.S. Cl.
CPC .......... *G06N 5/025* (2013.01); *G06F 16/258* (2019.01); *G06N 20/00* (2019.01)

(58) Field of Classification Search
CPC ....... G06N 5/025; G06N 20/00; G06F 16/258
See application file for complete search history.

(56) References Cited

U.S. PATENT DOCUMENTS

| | | | | |
|---|---|---|---|---|
| 8,924,415 | B2* | 12/2014 | Thomas | G06F 16/86 707/769 |
| 10,055,431 | B2* | 8/2018 | Marrelli | G06F 16/215 |
| 10,275,710 | B1* | 4/2019 | Teredesai | G06N 3/08 |
| 2012/0197907 | A1 | 8/2012 | Malyshev et al. | |
| 2014/0181128 | A1* | 6/2014 | Riskin | G06F 16/3344 707/756 |
| 2015/0026823 | A1 | 1/2015 | Ramesh et al. | |
| 2016/0063209 | A1* | 3/2016 | Malaviya | G16H 50/50 706/12 |
| 2016/0092475 | A1* | 3/2016 | Stojanovic | G06F 3/04883 707/805 |
| 2017/0243132 | A1* | 8/2017 | Sainani | G06N 20/00 |
| 2018/0314853 | A1* | 11/2018 | Oliner | G06F 21/6254 |

OTHER PUBLICATIONS

Alexe et al., "Designing and refining schema mappings via data examples," Proceedings of the 2011 ACM SIGMOD International Conference on Management of data, 12 pages.

* cited by examiner

*Primary Examiner* — Alexey Shmatov
*Assistant Examiner* — Robert Bejcek, II
(74) *Attorney, Agent, or Firm* — Patterson + Sheridan, LLP

(57) ABSTRACT

Performing an operation comprising transforming an input dataset to a predefined format, extracting, from the transformed dataset, a plurality of features describing the transformed dataset, and generating, by a machine learning (ML) algorithm executing on a processor and based on an ML model, a plurality of rules for modifying the transformed dataset to conform with a first data model.

17 Claims, 7 Drawing Sheets

FIG. 2A

```
MSH|^~\&|G|G|G|G|19990703||ADT^A04^ADT_A01|MSG.59|D|2.5
EVN||6||02
PID|1||text|123456789|Public^John^Q.^JR^Sir^^R||6^F|||long default text&abc^^Omaha^NY^10028^G||234-4532CWEEKENDS~(555)975-6478X4864~(555)975-4864~234-4532CWEEKENDS~(555)975-6478X4864^^^user@example.com|||||text|abc^G^200411
PV1||1|N|^G^G^^^G|A|||X^Moss^Robert~X^Beltran^Evan|X^Smith^Robert||||||||||||||9494984432|6|139.47|35.00||37.00
|||G|long default text|||||||||||||||||||||||||||||||
AL1||1|EA|12345^XYZABC^The patient is allergic to MSG from which he gets hives.|SV
```

(200, 201, 202 labels)

```
<primaryContact>
    <personID>123456789</personID>  ←——— 251
    <humanName>
        <given>John</given>
        <middle>Q.</middle>
        <nickName></nickName>
        <prefix>Sir</prefix>
        <suffix>JR</suffix>
        <surname>Public</surname>  ←——— 252
    </humanName>
    <sex>F</sex>
    <dateOfBirth></dateOfBirth>
    <city>Omaha</city>
    <state>NY</state>
    <street>long default text</street>
    <zipcode>10028</zipcode>
    <phone>(555)975-4864</phone>
    <email>user@example.com</email>
    <attendingDocID>long default text</attendingDocID>
    <attendingDocGivenName>Evan</attendingDocGivenName>
    <referringDocID>text</referringDocID>
    <referringDocGivenName>Robert</referringDocGivenName>
</primaryContact>
<allergies>  ←——— 253
    <entry>
        <key>keyClass</key>
        <value>
            <allergyId>12345</allergyId>
            <category/>
            <criticality>SV</criticality>
            <encounterId></encounterId>
            <lastOccurredAge>0</lastOccurredAge>
            <onsetAge>0</onsetAge>
            <description>The patient is allergic to MSG from which he gets hives.</description>
            <status></status>
            <substance/>
            <typeCode></typeCode>
        </value>
    </entry>
</allergies>
```

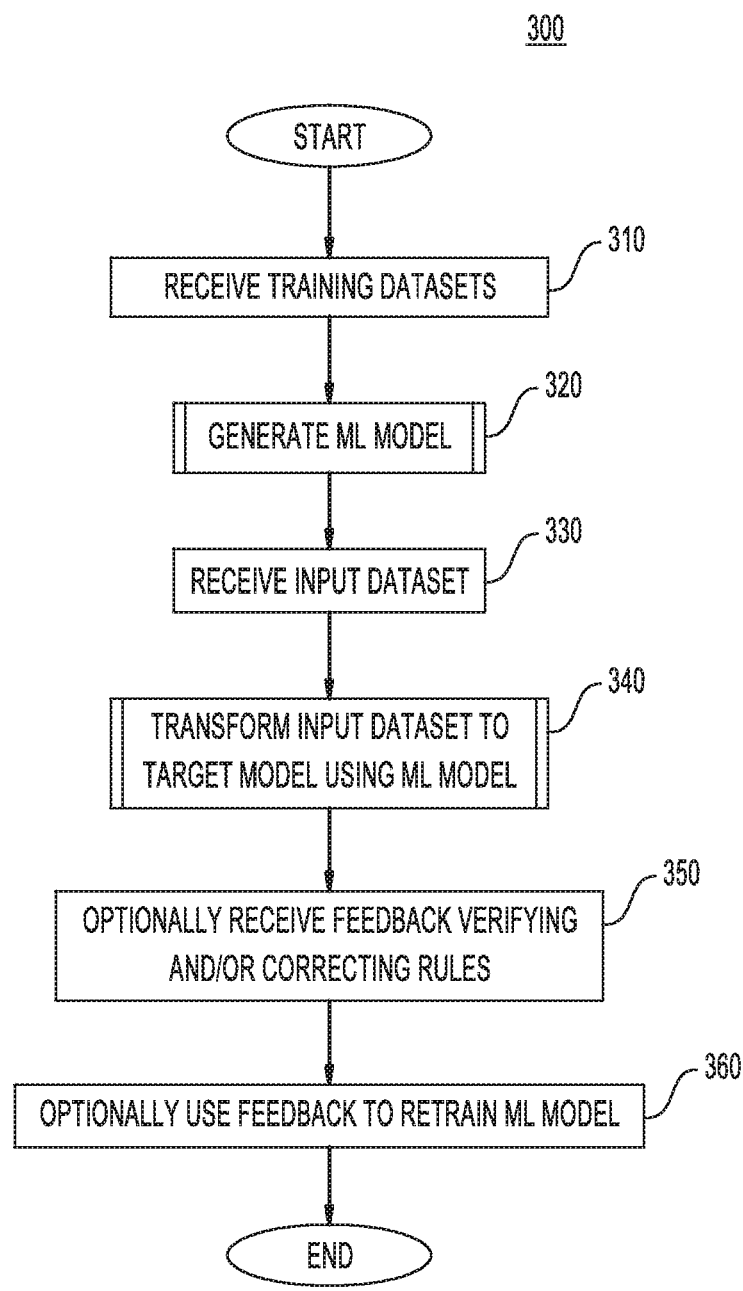

COGNITIVE DATA DISCOVERY AND MAPPING FOR DATA ONBOARDING

BACKGROUND

The present disclosure relates to computing, and more specifically, to providing cognitive data discovery and mappings for data onboarding.

Data can be formatted based on any number of standard and/or proprietary formats. However, service providers must provide a standard and unified interface for all clients to access data. As such, client data must be modified to the common format implemented by the service provider. Conventionally, this process involved manual onboarding of client data to map the data formats of each client to the common format implemented by the service provider. This manual onboarding process is time consuming, and requires hundreds of people to repeat the process for each new client.

SUMMARY

According to one embodiment, a method comprises transforming an input dataset to a predefined format, extracting, from the transformed dataset, a plurality of features describing the transformed dataset, and generating, by a machine learning (ML) algorithm executing on a processor and based on an ML model, a plurality of rules for modifying the transformed dataset to conform with a first data model.

In another embodiment, a system comprises a processor and a memory storing instructions, which when executed by the processor, performs an operation comprising transforming an input dataset to a predefined format, extracting, from the transformed dataset, a plurality of features describing the transformed dataset, and generating, by a machine learning (ML) algorithm executing on a processor and based on an ML model, a plurality of rules for modifying the transformed dataset to conform with a first data model.

In another embodiment, a computer-readable storage medium has computer-readable program code embodied therewith, the computer-readable program code executable by a processor to perform an operation comprising transforming an input dataset to a predefined format, extracting, from the transformed dataset, a plurality of features describing the transformed dataset, and generating, by a machine learning (ML) algorithm executing on a processor and based on an ML model, a plurality of rules for modifying the transformed dataset to conform with a first data model.

BRIEF DESCRIPTION OF THE SEVERAL VIEWS OF THE DRAWINGS

FIGS. 2A-2B illustrate data that is processed using cognitive data discovery and mappings, according to one embodiment.

FIG. 3 is a flow chart illustrating a method for cognitive data discovery and mappings for data onboarding, according to one embodiment.

DETAILED DESCRIPTION

Embodiments disclosed herein provide techniques to process any input data source using deep learning to transform the input data source to a target data model. The input data source may be of any type and/or format, such as a structured data source, unstructured data source, standardized data source, proprietary data source, and the like. In a training phase, one or more machine learning (ML) models are generated based on different training data sources. The ML models may be associated with one or more target data models having a predefined format. Once trained, the ML models may be used to generate rules, mappings, translations, and/or other modifications to convert an input data source to the target data model.

Figure 1:
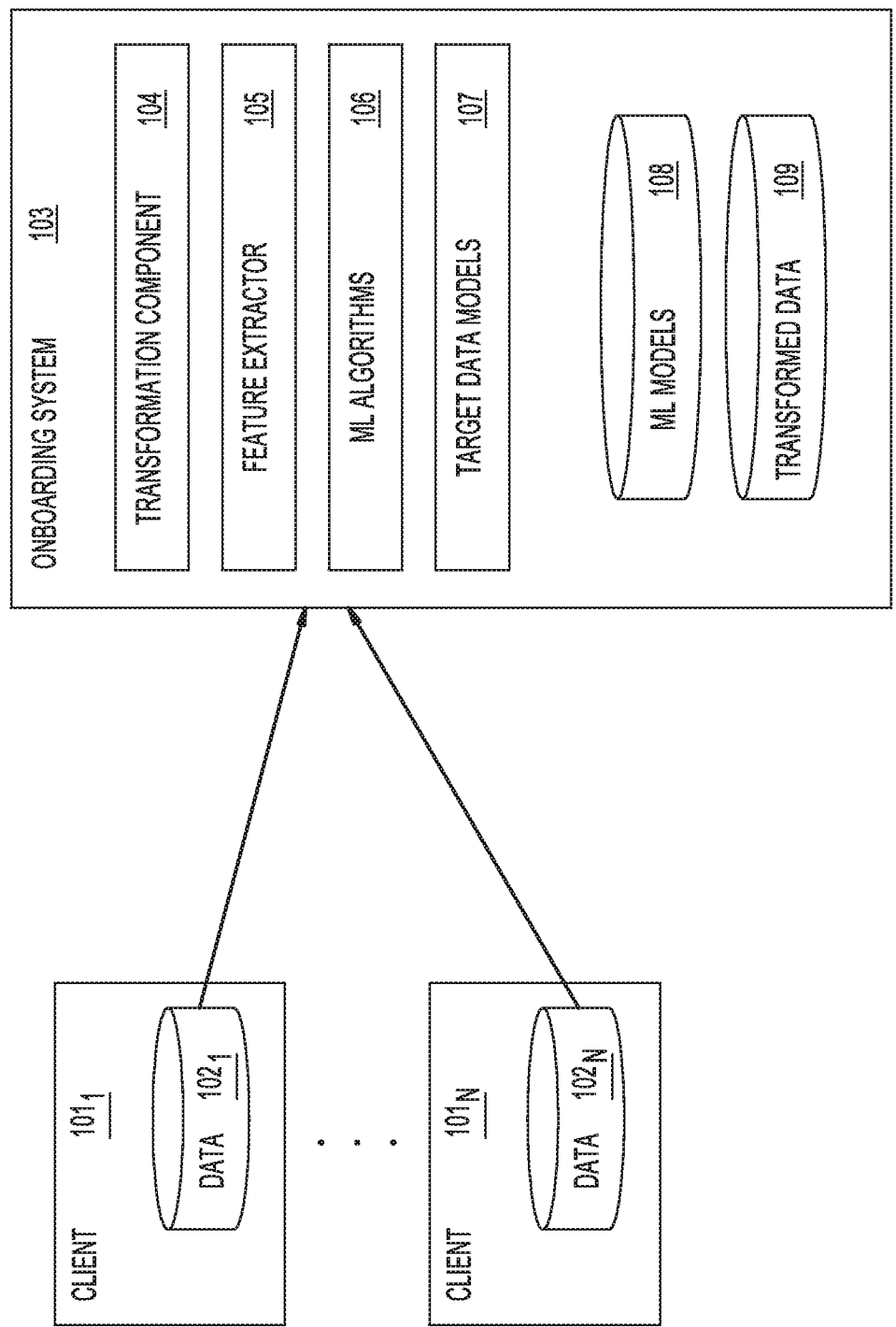
FIG. 1 illustrates a system which implements cognitive data discovery and mappings for data onboarding, according to one embodiment.

FIG. 1 illustrates a system 100 which implements cognitive data discovery and mappings for data onboarding, according to one embodiment. As shown, the system 100 includes one or more client systems $101_{1-N}$ and an onboarding system 103. The client systems $101_{1-N}$ include client data stores $102_{1-N}$. In at least one embodiment, the data stores $102_{1-N}$ includes health data, e.g., patient data, medical provider data, insurance data, etc. The data stores $102_{1-N}$ may include data that is in any type of format, including unformatted data. For example, and without limitation, the data stores $102_{1-N}$ may include unstructured data, structured data, data that is formatted according to one or more standards, and/or data that is formatted according to one or more proprietary formats.

As shown, the onboarding system 103 includes a transformation component 104, a feature extractor 105, one or more machine learning (ML) algorithms 106, one or more target data models 107, one or more ML models 108, and one or more data stores for transformed data 109. The onboarding system 103 is generally configured to convert the data in the client data stores $102_{1-N}$ according to one or more target data models 107. To convert the client data $102_{1-N}$, the onboarding system 103 may generate one or more rules (also referred to as mappings) for converting the client data $102_{1-N}$ to a target data model 107. The target data models 107 are representative of any type of data model, such as the IBM® Unified Data Model (UDMH). Generally, a data model is an abstract model that organizes elements of data and standardizes how they relate to one another and/or to properties of the real world entities. For example, an enterprise managing the client data $102_1$ may be a new client of an enterprise including the onboarding system 103. The client data $102_1$ may be unstructured and/or unformatted, while the enterprise managing the onboarding system 103 may need to convert the client data $102_1$ to a predefined format defined by a target data model 107. To convert the client data $102_1$ to the target data model 107, the onboarding system 103 may, for example, generate a rule which transforms the first N bytes of each data record in the client data $102_1$ to a patient last name formatted according to a last name format defined in the target data model 107. Similarly, the onboarding system 103 may generate a rule which maps a "patient_data" database table in the client data $102_1$ to a "patientdata" table for patient data defined by the target data model 107.

To onboard the client data $102_{1-N}$, the onboarding system 103 may initially analyze the client data $102_{1-N}$ to identify any attributes of the client data $102_{1-N}$. For example, the onboarding system 103 may determine a database schema defined in the client data $102_{1-N}$, a format of the client data $102_{1-N}$, and/or determine any other identifiable attribute of the client data $102_{1-N}$. The transformation component 104 may then transform the data in the client data $102_{1-N}$ to a common, structured format, such as the extensible markup language (XML). The feature extractor 105 may then extract features of the client data $102_{1-N}$. Generally, a feature is an attribute of the client data $102_{1-N}$. For example, the feature extractor 105 may include natural language processing (NLP) algorithms which identify context features (e.g., what is the context of a given data record, identify sentiment, etc.), identify grammatical features (e.g., generate a parse tree for the data), and identify what type of data is stored in a given record of the client data $102_{1-N}$ (e.g., identify patient identifiers, names, medical conditions, etc.). For example, the feature extractor 105 may generate a feature vector for the client data $102_{1-N}$ which identifies the data types in a data record, dependencies between terms, relationships between terms, and the like. The feature extractor 105 may further generate annotations which are applied to the text of the client data $102_{1-N}$. For example, the feature extractor 105 may annotate a sentence "John Q. Public, 100 Main Street, Anytown, USA" with annotations indicating that the sentence includes the patient's name and address.

The client data $102_{1-N}$, output of the feature extractor 105 (e.g., extracted features, annotations, parse trees, etc.), and the target data model 107 may then be provided as input to one or more ML algorithms 106 to generate one or more rules, or mappings, to convert the client data $102_{1-N}$ to the target data model 107. The ML algorithms 106 are representative of any type of learning algorithm, such as neural networks, deep learning algorithms, classifiers, clustering algorithms, decision trees, support vector machines, and the like. The ML algorithms 106 may apply one or more ML models 108, which generates one or more rules for converting data in the client data $102_{1-N}$ to conform with the target data model 107. For example, a first rule, or mapping, may specify to convert data in the client data $102_1$ that has 9 digits separated by "&" (e.g., "1&2&3&4&5&6&7&8&9") to a 9 digit numeric patient ID defined in the target data model 107. The onboarding system 103 may then apply the generated rules to the client data $102_{1-N}$ to convert the client data $102_{1-N}$, which may be stored as transformed data 109 that is formatted according to the target data model 107.

The ML models 108 are representative of any type of machine learning model, and may store any rules and/or mappings for converting client data $102_{1-N}$ to a target data model 107. The ML models 108 are generated by one or more ML algorithms 106 during a training phase based on training data. In at least one embodiment, the training data includes the client data $102_{1-N}$. During the training phase, the ML algorithms 106 may process the training data, any existing mappings (e.g., defined in existing ML models 108 and/or the target data model 107), and the target data model 107 to generate the ML model 108. The generated ML model 108 may include, without limitation, rules for mapping client data $102_{1-N}$ to the target data model 107. Once generated, the ML model 108 can be used to convert new and/or existing client data $102_{1-N}$ to the associated target data model 107.

In at least one embodiment, the onboarding system 103 may output rules generated to a user for review. The user may then accept the rules, modify the rules, and/or reject the rules. The feedback provided by the user may then be used to retrain the ML models 108, which in turn improves the accuracy of subsequent rules generated by the ML models 108. Advantageously, the system 100 allows client data $102_{1-N}$ to be onboarded in a completely automated fashion, while allowing for changes to the client data $102_{1-N}$ and/or the target data models 107.

FIG. 2A illustrates an example data record 200 from client data $102_{1-N}$ that is processed using cognitive data discovery and mappings, according to one embodiment. As shown, the data record 200 includes numerous symbols (e.g., "1", "A", etc.) interleaved in patient data. To onboard the data record 200, the onboarding system 103 may analyze the data record 200 to identify any attributes thereof. For example, by identifying the header "MSH" in the data record 200, the onboarding system 103 may determine that the data record 200 is a Health Level-7® (HL7®) message. The onboarding system 103 may then invoke the transformation component 104, which converts the data record 200 to temporary standard format (e.g., by removing symbols, headers, etc.). The onboarding system 103 may then invoke the feature extractor 105, which extracts features from the data record 200. For example, the feature extractor 105 may apply an NLP algorithm which identifies the concept "allergic" in the data record 200, and determine that the concept of "allergic" is dependent on the term "MSG". The feature extractor 105 may then annotate the data record 200 with an annotation reflecting that an allergy of the patient is specified, and that the patient is allergic to MSG. The onboarding system 103 may then provide the data record 200, a target data model 107, and a ML model 108 associated with the selected target data model 107 to the ML algorithm 106 for processing. The ML algorithm 106 may then generate one or more rules for converting the data record 200 to comply with the target data model 107. For example, a first rule may specify that element 201 of the data record 200 corresponds to a patient identifier, and should be formatted according to a format for patient identifiers specified in the target data model 107. As another example, a second rule may specify that element 202 of the data record 200 corresponds to the patient's last name, and should be formatted according to a format for last names specified in the target data model 107. The onboarding system 103 may then optionally convert the data record 200 using the generated rules, and store the converted data record in the transformed data 109.

FIG. 2B depicts a data record 250, which corresponds to the data record 200 of FIG. 2A that has been converted to a target data format 107. In this example, the target data format 107 is the Common Standard Input Format (SIF), an XML interchange format. As such, the relevant data of the data record 200 has been identified and mapped to the target data format 107. For example, as shown, data element 251 includes an identifier formatted according to the "<personID>" tag, while data element 252 includes a person's last name formatted according to the "<surname>" tag. Furthermore, as shown, based on the statement "The patient is allergic to MSG from which he gets hives", an "<allergies>" tag 253 has been defined, with the relevant patient allergy attributes extracted from the data record 200 and stored in the data record 250 according to the target data format 107.

FIG. 3 is a flow chart illustrating a method 300 for cognitive data discovery and mappings for data onboarding, according to one embodiment. As shown, the method 300 begins at block 310, where the onboarding system 103 receives one or more training datasets. The training datasets may include structured data and/or unstructured data, where the structured data is structured according to any number and/or type of format. At block 320, described in greater detail with reference to FIG. 4, where the onboarding system 103 generates one or more ML models 108 during a training phase of one or more ML algorithms 106. The ML models 108 may be specific to one or more target data models 107, and include rules for converting client data $102_{1-N}$ to the corresponding target data models 107.

At block 330, the onboarding system 103 receives an input dataset, such as a client data $102_{1-N}$ from one or more clients. At block 340, described in greater detail with reference to FIG. 4, the onboarding system 103 transforms the input dataset to the target data model 107 using one or more ML models 108. As previously stated, the onboarding system 103 transforms the input dataset to a common format, extracts features from the input dataset, and applies the ML model 108 to define a rule (or select an existing rule) for modifying the input dataset to conform with the requirements of the target data model 107. At block 350, the onboarding system 103 optionally receives user feedback verifying, rejecting, and/or correcting one or more rules for transforming (or mapping) the input dataset to the target data model generated at block 340. At block 360, the onboarding system 103 uses the received feedback to retrain the ML models 108.

Figure 4:
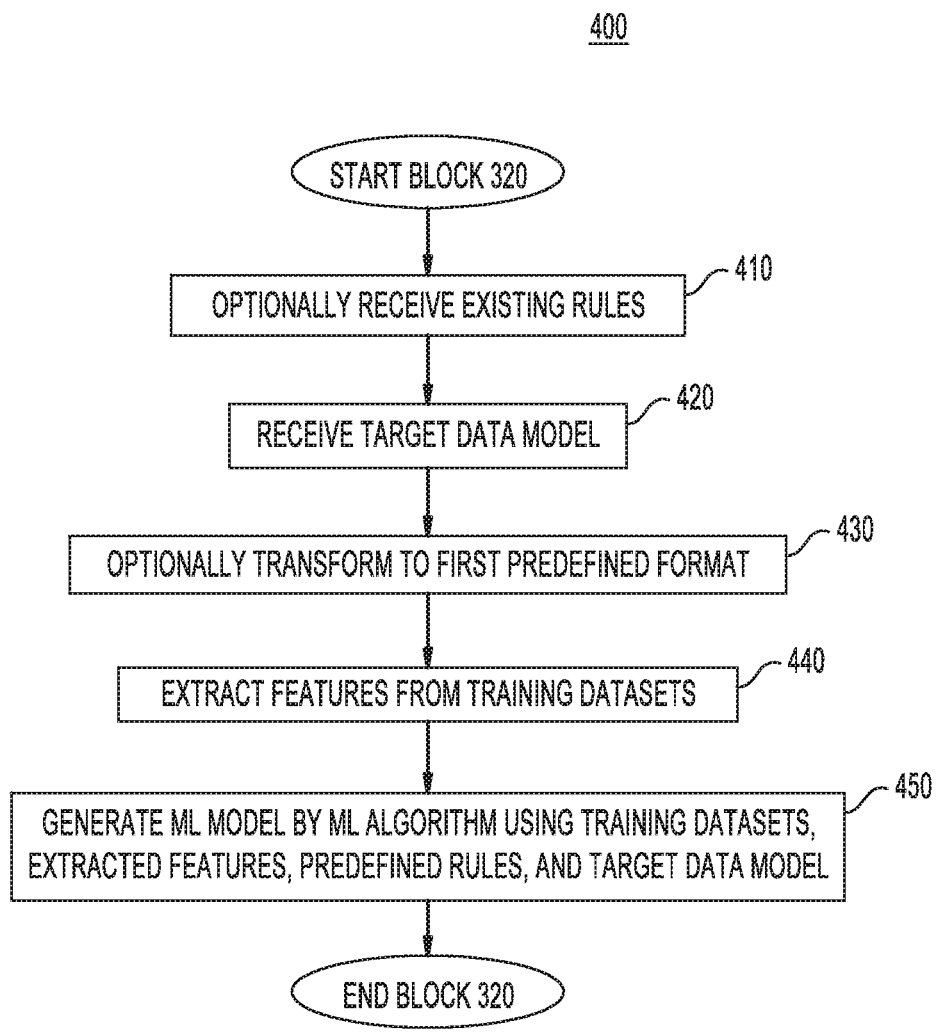
FIG. 4 is a flow chart illustrating a method to generate a machine learning model, according to one embodiment.

FIG. 4 is a flow chart illustrating a method 400 corresponding to block 320 to generate a machine learning model, according to one embodiment. As shown, the method 400 begins at block 410, where the onboarding system 103 optionally receives existing rules, including predefined rules, and/or rules that have been defined during a previous training session of the ML algorithms 106 and stored in the ML models 108. At block 420, the onboarding system 103 receives selection of a target data model 107 (e.g., UDMH). At block 430, the transformation component 104 optionally transforms the training data to a first predefined format (e.g. XML). At block 440, the feature extractor 105 extracts features from the training datasets. As previously stated, the feature extractor 105 may extract context features, sentiment features, and grammatical features, and generate parse trees, feature vectors, and annotations for the training datasets. At block 450, an ML algorithm 106 generates a ML model 108 based on the existing mappings, selected target data model 107, the extracted features, and the training datasets. The onboarding system 103 may then store the ML model 108 for later use.

Figure 5:
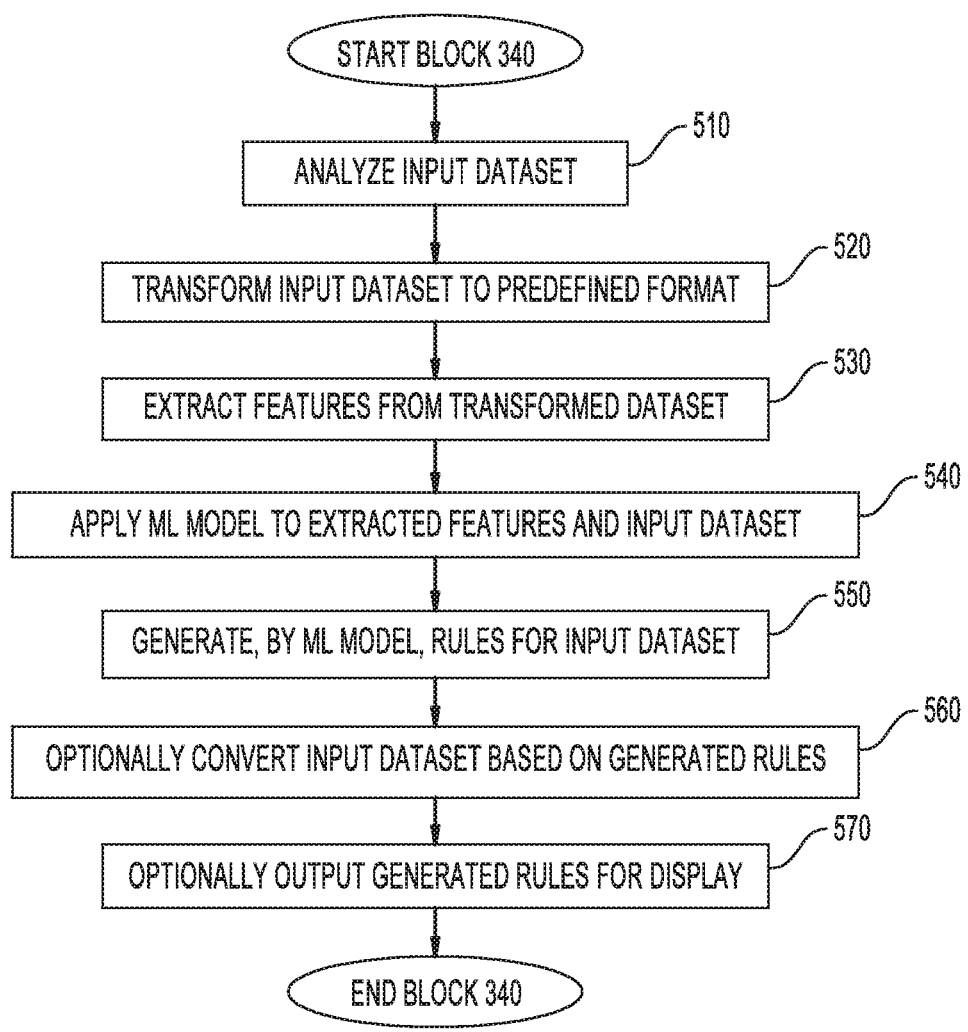
FIG. 5 is a flow chart illustrating a method to transform an input dataset to a target model using a machine learning model, according to one embodiment.

FIG. 5 is a flow chart illustrating a method 500 corresponding to block 340 to transform an input dataset to a target model using a machine learning model, according to one embodiment. As shown, the method 500 begins at block 510, where the onboarding system 103 analyzes the input dataset, e.g., to identify a type of the input dataset, formatting, schemas, and/or other attributes. At block 320, the transformation component 105 transforms the input dataset to a predefined format for further processing. At block 530, the feature extractor 105 extracts features from the input dataset. For example, the feature extractor 105 may extract features describing the context of sentences in the input dataset, features describing sentiment in sentences in the input dataset, and grammatical features describing the grammar of text in the input dataset. The feature extractor 105 may further generate parse trees, feature vectors, and annotations for the input dataset.

At block 540, the ML algorithm 106 applies an ML model 108 to the input dataset. More generally, the ML algorithm 106 receives the input dataset, the target data model 107, any existing rules as input, which processes the input based on the ML model 108. At block 550, the ML model 108 and/or ML algorithm 106 generates one or more rules for transforming the input dataset (and/or identifies one or more existing rules for transforming the input dataset). At block 560, the onboarding system 103 optionally converts the input dataset based on the generated rules, and stores the results as the transformed data 109. At block 570, the onboarding system 103 optionally outputs the generated rules to a user for display. The user may then modify the rules, accept the rules, and/or reject the rules. As previously stated, the rules may include transformation rules, mapping rules, and any other type of operation for modifying and/or mapping data from the input dataset to a target data model 107.

Figure 6:
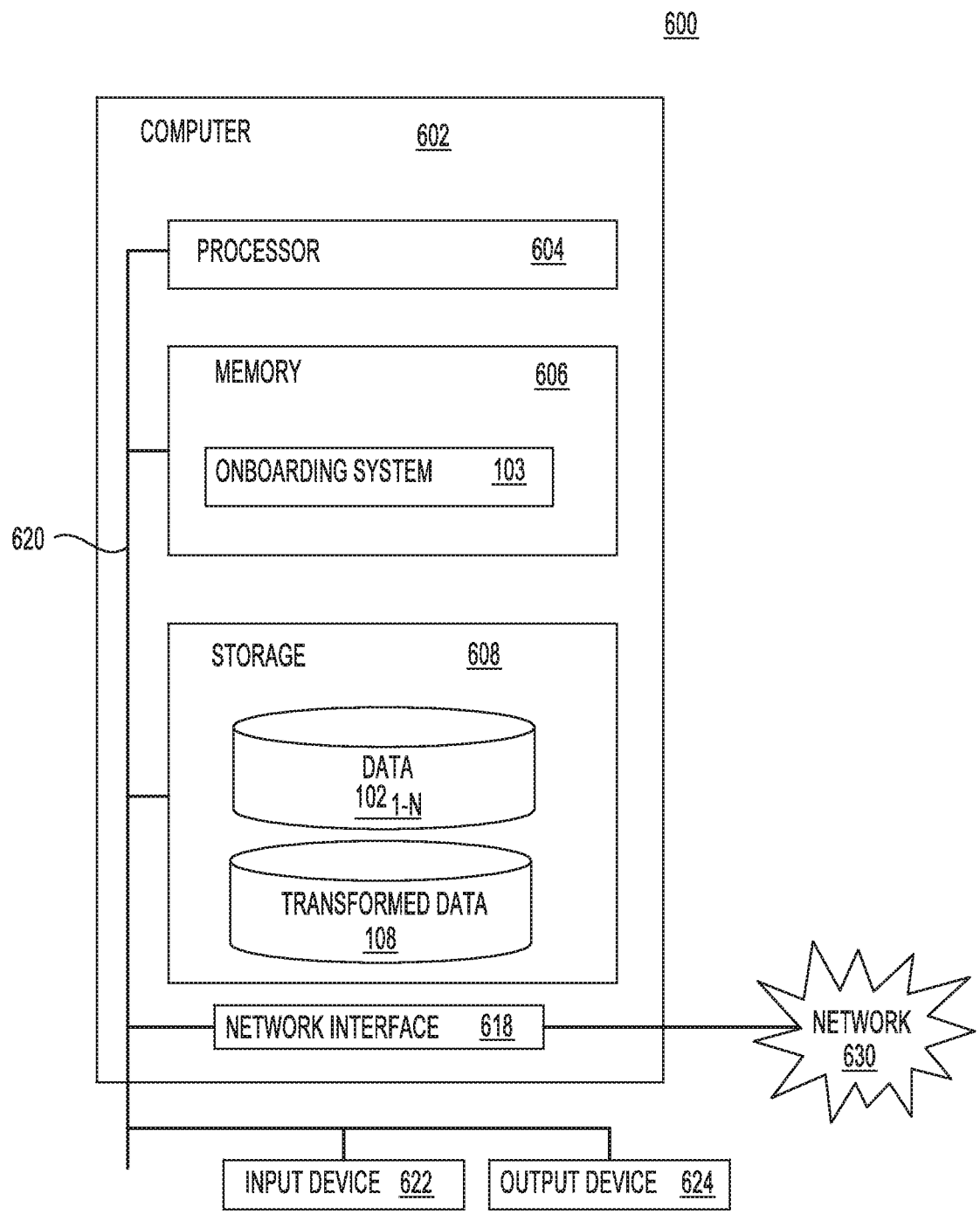
FIG. 6 illustrates a system which implements cognitive data discovery and mappings for data onboarding, according to one embodiment.

FIG. 6 illustrates a system 600 which implements cognitive data discovery and mappings for data onboarding, according to one embodiment. The networked system 600 includes a computing system 602. The computing system 602 may also be connected to other computers via a network 630. In general, the network 630 may be a telecommunications network and/or a wide area network (WAN). In a particular embodiment, the network 630 is the Internet.

The computing system 602 generally includes a processor 604 which obtains instructions and data via a bus 620 from a memory 606 and/or a storage 608. The computing system 602 may also include one or more network interface devices 618, input devices 622, and output devices 624 connected to the bus 620. The computing system 602 is generally under the control of an operating system (not shown). Examples of operating systems include the UNIX operating system, versions of the Microsoft Windows operating system, and distributions of the Linux operating system. (UNIX is a registered trademark of The Open Group in the United States and other countries. Microsoft and Windows are trademarks of Microsoft Corporation in the United States, other countries, or both. Linux is a registered trademark of Linus Torvalds in the United States, other countries, or both.) More generally, any operating system supporting the functions disclosed herein may be used. The processor 604 is a programmable logic device that performs instruction, logic, and mathematical processing, and may be representative of one or more CPUs. The network interface device 618 may be any type of network communications device allowing the computing system 602 to communicate with other computers via the network 630.

The storage 608 is representative of hard-disk drives, solid state drives, flash memory devices, optical media and the like. Generally, the storage 608 stores application programs and data for use by the computing system 602. In addition, the memory 606 and the storage 608 may be considered to include memory physically located elsewhere; for example, on another computer coupled to the computing system 602 via the bus 620.

The input device 622 may be any device for providing input to the computing system 602. For example, a keyboard and/or a mouse may be used. The input device 622 represents a wide variety of input devices, including keyboards, mice, controllers, and so on. Furthermore, the input device 622 may include a set of buttons, switches or other physical device mechanisms for controlling the computing system 602. The output device 624 may include output devices such as monitors, touch screen displays, and so on.

As shown, the memory 606 contains the onboarding system 103, described in greater detail above. As shown, the storage 608 includes the client data $102_{1-N}$, and the transformed data 108, each described in greater detail above. Generally, the system 600 is configured to implement all systems, methods, and functionality described above with reference to FIGS. 1-5. Advantageously, the performance of the computer 602 is improved by providing an onboarding system 103 which can convert any type of data to a target data model 107 without having to be explicitly programmed to do so.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the foregoing, reference is made to embodiments presented in this disclosure. However, the scope of the present disclosure is not limited to specific described embodiments. Instead, any combination of the recited features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the recited aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Embodiments of the invention may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present invention, a user may access applications or related data available in the cloud. For example, the onboarding system 103 could execute on a computing system in the cloud and transform client data to conform with a target data model. In such a case, the onboarding system 103 could transform the client data and store the transformed data at a storage location in the cloud. Doing so allows a user to access this information from any computing system attached to a network connected to the cloud (e.g., the Internet).

While the foregoing is directed to embodiments of the present invention, other and further embodiments of the invention may be devised without departing from the basic scope thereof, and the scope thereof is determined by the claims that follow.

What is claimed is:

1. A method, comprising:
receiving a plurality of training datasets, each training dataset comprising structured data and unstructured data;
receiving an indication of a first data model to be used as a target for transforming the plurality of training datasets;
generating a machine learning (ML) model to generate rules to transform input data to the first data model, based on the plurality of training datasets;
transforming an input dataset to a predefined temporary format;
extracting, from the transformed input dataset in the predefined temporary format, a plurality of features describing the transformed input dataset in the predefined temporary format, comprising:
identifying contextual features of a given data record using natural language processing;
identifying a sentiment using natural language processing;
identifying grammatical features by generating a parse tree;
identifying types of data stored in the given data record, comprising identifying a patient identifier, name, and medical conditions included in the given data record;
determining data dependencies between concepts in the given data record, wherein at least one of the data dependencies is determined by using one or more natural language processing (NLP) algorithms, and wherein the at least one of the data dependencies indicates that a first concept corresponding to allergies is dependent on a second concept corresponding to a specific allergen in the given data record; and
generating annotations indicating content of the given data record;
generating, by processing the plurality of features using a machine learning (ML) algorithm executing on a processor and based on the ML model comprising a support vector machine, a plurality of rules for modifying the input dataset to conform with a first data model, wherein:
a first rule of the plurality of rules specifies to transform a specific and fixed number of bytes at a beginning of each data record in the input dataset to a specific field and formatted according to a specific format specified in the first data model, and
a second rule of the plurality of rules specifies to transform data comprising a fixed number of digits, separated by ampersand characters, to an identifier field specified in the first data model; and
transforming the input dataset to the first data model using the plurality of rules.

2. The method of claim 1, further comprising:
modifying the input dataset based on the plurality of rules to conform with the first data model; and
storing the modified input dataset.

3. The method of claim 1, further comprising prior to transforming the input dataset to the predefined format:
receiving at least one existing rule for modifying datasets; and
generating, based further on the at least one existing rule, the ML model.

4. The method of claim 1, further comprising:
receiving the input dataset; and
determining, based on an analysis of the input dataset, at least one attribute of the input dataset.

5. The method of claim 1, further comprising:
outputting the plurality of rules for display;
receiving feedback for at least a first rule of the plurality of rules; and
retraining the ML model based on the received feedback.

6. The method of claim 1, wherein the input dataset comprises health data, wherein the input dataset comprises one or more of: (i) unstructured data, and (ii) structured data formatted according to one of a plurality of predefined formats.

7. A computer program product, comprising:
a non-transitory computer-readable storage medium having computer readable program code embodied therewith, the computer readable program code executable by a processor to perform an operation comprising:
receiving a plurality of training datasets, each training dataset comprising structured data and unstructured data;
receiving an indication of a first data model to be used as a target for transforming the plurality of training datasets;
generating a machine learning (ML) model to generate rules to transform input data to the first data model, based on the plurality of training datasets;
transforming an input dataset to a predefined temporary format;
extracting, from the transformed input dataset in the predefined temporary format, a plurality of features describing the transformed input dataset in the predefined temporary format, comprising:
identifying contextual features of a given data record using natural language processing;
identifying a sentiment using natural language processing;
identifying grammatical features by generating a parse tree;
identifying types of data stored in the given data record, comprising identifying a patient identifier, name, and medical conditions included in the given data record;
determining data dependencies between concepts in the given data record, wherein at least one of the data dependencies is determined by using one or more natural language processing (NLP) algorithms, and wherein the at least one of the data dependencies indicates that a first concept corresponding to allergies is dependent on a second concept corresponding to a specific allergen in the given data record; and
generating annotations indicating content of the given data record;
generating, by processing the plurality of features using a machine learning (ML) algorithm executing on a processor and based on the ML model comprising a support vector machine, a plurality of rules for modifying the transformed input dataset to conform with a first data model, wherein:
a first rule of the plurality of rules specifies to transform a specific and fixed number of bytes at a beginning of each data record in the input dataset to a specific field and formatted according to a specific format specified in the first data model, and
a second rule of the plurality of rules specifies to transform data comprising a fixed number of digits, separated by ampersand characters, to an identifier field specified in the first data model; and
transforming the input dataset to the first data model using the plurality of rules.

8. The computer program product of claim 7, the operation further comprising:
modifying the input dataset based on the plurality of rules to conform with the first data model; and
storing the modified input dataset.

9. The computer program product of claim 7, the operation further comprising prior to transforming the input dataset to the predefined format:
receiving at least one existing rule for modifying datasets; and
generating, based further on the at least one existing rule, the ML model.

10. The computer program product of claim 7, the operation further comprising:
receiving the input dataset; and
determining, based on an analysis of the input dataset, at least one attribute of the input dataset.

11. The computer program product of claim 7, the operation further comprising:
outputting the plurality of rules for display;
receiving feedback for at least a first rule of the plurality of rules; and
retraining the ML model based on the received feedback.

12. The computer program product of claim 7, wherein the input dataset comprises health data, wherein the input dataset comprises one or more of: (i) unstructured data, and (ii) structured data formatted according to one of a plurality of predefined formats.

13. A system, comprising:
a processor; and
a memory storing one or more instructions which, when executed by the processor, performs an operation comprising:
receiving a plurality of training datasets, each training dataset comprising structured data and unstructured data;
receiving an indication of a first data model to be used as a target for transforming the plurality of training datasets;
generating a machine learning (ML) model to generate rules to transform input data to the first data model, based on the plurality of training datasets;
transforming an input dataset to a predefined temporary format;
extracting, from the transformed input dataset in the predefined temporary format, a plurality of features describing the transformed input dataset in the predefined temporary format, comprising:
identifying contextual features of a given data record using natural language processing;
identifying a sentiment using natural language processing;
identifying grammatical features by generating a parse tree;
identifying types of data stored in the given data record, comprising identifying a patient identifier, name, and medical conditions included in the given data record;
determining data dependencies between concepts in the given data record, wherein at least one of the data dependencies is determined by using one or more natural language processing (NLP) algorithms, and wherein the at least one of the data dependencies indicates that a first concept corresponding to allergies is dependent on a second concept corresponding to a specific allergen in the given data record; and generating annotations indicating content of the given data record;

generating, by processing the plurality of features using a machine learning (ML) algorithm executing on a processor and based on the ML model comprising a support vector machine, a plurality of rules for modifying the transformed input dataset to conform with a first data model, wherein:
- a first rule of the plurality of rules specifies to transform a specific and fixed number of bytes at a beginning of each data record in the input dataset to a specific field and formatted according to a specific format specified in the first data model, and
- a second rule of the plurality of rules specifies to transform data comprising a fixed number of digits, separated by ampersand characters, to an identifier field specified in the first data model; and transforming the input dataset to the first data model using the plurality of rules.

14. The system of claim 13, the operation further comprising:
modifying the input dataset based on the plurality of rules to conform with the first data model; and
storing the modified input dataset.

15. The system of claim 13, the operation further comprising prior to transforming the input dataset to the predefined format:
receiving at least one existing rule for modifying datasets; and
generating, further on the at least one existing rule, the ML model.

16. The system of claim 13, the operation further comprising:
receiving the input dataset; and
determining, based on an analysis of the input dataset, at least one attribute of the input dataset.

17. The system of claim 13, wherein the input dataset comprises health data, wherein the input dataset comprises one or more of: (i) unstructured data, and (ii) structured data formatted according to one of a plurality of predefined formats, wherein the operation further comprises:
outputting the plurality of rules for display;
receiving feedback for at least a first rule of the plurality of rules; and
retraining the ML model based on the received feedback.

* * * * *